(12) United States Patent
Yar

(10) Patent No.: US 9,169,221 B2
(45) Date of Patent: Oct. 27, 2015

(54) DIHYDRO 1,4-BENZOXAZINES AND METHOD OF SYNTHESIZING THE SAME USING SULFONIUM SALTS

(71) Applicant: COMSATS Institute of Information Technology, Lahore (PK)

(72) Inventor: Muhammad Yar, Lahore (PK)

(73) Assignee: COMSATS Institute of Information Technology, Lahore (PK)

( * ) Notice: Subject to any disclaimer, the term of this patent is extended or adjusted under 35 U.S.C. 154(b) by 0 days.

(21) Appl. No.: 14/041,978

(22) Filed: Sep. 30, 2013

(65) Prior Publication Data

US 2014/0323720 A1   Oct. 30, 2014

(30) Foreign Application Priority Data

Apr. 29, 2013 (PK) ..................... 262/2013

(51) Int. Cl.
*C07D 265/36* (2006.01)
(52) U.S. Cl.
CPC .................. *C07D 265/36* (2013.01)
(58) Field of Classification Search
CPC .................................................. C07D 265/36
USPC ....................................... 544/105
See application file for complete search history.

(56) References Cited

PUBLICATIONS

Turbanti et al. Chim. Ther. (1967), 2(5), 354-365.*
Chacun-Lefevre et al. Tetrahedron Letters (1998), 39(32), 5763-5764.*

* cited by examiner

*Primary Examiner* — Kahsay Habte
(74) *Attorney, Agent, or Firm* — H.C. Park & Associates, PLC

(57) ABSTRACT

Exemplary embodiments of the present invention relate to benzoxazines having various N-protecting groups. An $R_1$ functional group is at least one selected from the group consisting of H and a halogen, an $R_2$ functional group is at least one selected from the group consisting of H, an amide, or a carbamate, and a Z functional group is at least one selected from the group consisting of a phenyl, substituted phenyl group, methyl, and t-butyl group. The exemplary embodiments provide compounds with benzoxazines having various cleavable protecting groups such as amides and carbamates.

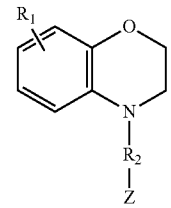

6 Claims, No Drawings

DIHYDRO 1,4-BENZOXAZINES AND METHOD OF SYNTHESIZING THE SAME USING SULFONIUM SALTS

CROSS-REFERENCE TO RELATED APPLICATION

This application claims priority from and the benefit of Pakistani Patent Application No. 262/2013, filed on Apr. 29, 2013, which is incorporated by reference for all purposes as if set forth herein.

BACKGROUND

1. Field

Exemplary embodiments of the present invention relate to benzoxazines having various N-protecting groups.

2. Discussion of the Background

Benzoxazine derivatives have been known to exhibit interesting pharmacological properties, and 3,4-dihydro benzoxazine derivatives may be antibacterial agents, and are may be an integral part of URAT inhibitors. 1,4-benzoxazine (ABO) may promote angiogenesis in vivo and in vitro. A benzoxazine derivative, (6-tert-butyl-3,4-dihydro-2H-benzo[b][1,4]oxazin-3-yl)-methanol (TBM) may act as a cell growth inhibitor that inhibits the proliferation of p53 wild-type lung adenocarcinoma cells. 5-Hydroxytryptamine (5-HT6) receptor messenger RNA (mRNA) may occupy high level of receptors in the brain, which mediates the actions of the neurotransmitter 5-hydroxytryptamine (5-HT). Benzoxazine derivatives may be used for modulating (5-HT) receptors, especially 5-HT, which may be useful for the treatment of several central nervous system disorders such as Parkinson disease, anxiety, depression, epilepsy, Alzheimer disease, sleep disorders, attention deficit disorder (ADD), and attention deficit hyperactivity disorder (ADHD).

The direct synthesis of compounds from 1,2-diahalo derivatives may suffer from low yields, and a three step sequence synthesis may be adopted using α-haloesters as an alkylating agent followed by alkylation, ring closing, and finally a reduction step to furnish the required products. Previously, the synthesis of a range of pharmacologically important heterocyclic compounds, from β-amino alcohols and a diphenyl vinyl sulfonium salt, in good yields, has been reported. Although a range of amino substituents may work effectively, including sulfonamides, sulfinamides, aromatic, and heteroaromatic groups, carbonyl based protecting groups such as amides and carbamates have failed under similar conditions.

The above information disclosed in this Background section is only for enhancement of understanding of the background of the invention and, therefore, it may contain information that does not form any part of the prior art nor what the prior art may suggest to a person of ordinary skill in the art.

SUMMARY OF THE INVENTION

Exemplary embodiments of the present invention provide benzoxazines having various N-protecting groups, such as amides, butyloxycabonyl-carbamate (BOC-carbamate), benzyloxycarbonyl-carbamate (Cbz-carbamate), and un-protected benzoxazines, and methods of synthesizing the same.

Exemplary embodiments of the present invention also provide for methods of synthesizing biologically important benzoxazines in high yields and under mild reaction conditions.

Additional features of the invention will be set forth in the description which follows, and in part will be apparent from the description, or may be learned by practice of the invention.

An exemplary embodiment of the present invention discloses a compound having the formula (I):

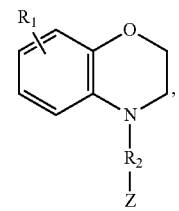

wherein R1 is at least one selected from the group consisting of H and a halogen, R2 is at least one selected from the group consisting of H, an amide, and a carbamate, and Z is at least one selected from the group consisting of a phenyl, a substituted phenyl, a methyl, and a t-butyl.

An exemplary embodiment of the present invention also discloses a method of preparing a compound of formula (I), the method including reacting a substituted amino phenol with a bromoethyl sulfonium triflate in the presence of at least one base, the base selected from the group consisting of sodium hydride, 1,8-diazabicyclo[5.4.0]undec-7-ene (DBU), and sodium tertiary butoxide, in at least one solvent selected from the group consisting of dicholoromethane, tetrahydrofuran, chloroform, and acetonitrile, at a temperature in the range of 25 to 30° C.

It is to be understood that both the foregoing general description and the following detailed description are exemplary and explanatory and are intended to provide further explanation of the invention as claimed.

DETAILED DESCRIPTION OF THE ILLUSTRATED EMBODIMENTS

In the following description, for the purposes of explanation, numerous specific details are set forth in order to provide a thorough understanding of various exemplary embodiments. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments.

It will be understood that when an element or layer is referred to as being "on" or "connected to" another element or layer, it can be directly on or directly connected to the other element or layer, or intervening elements or layers may be present. In contrast, when an element is referred to as being "directly on" or "directly connected to" another element or layer, there are no intervening elements or layers present. It will be understood that for the purposes of this disclosure, "at least one of X, Y, and Z" can be construed as X only, Y only, Z only, or any combination of two or more items X, Y, and Z (e.g., XYZ, XYY, YZ, ZZ).

In the accompanying figures, the size and relative sizes of layers, films, panels, regions, etc., may be exaggerated for clarity and descriptive purposes. Also, like reference numerals denote like elements.

Compounds of exemplary embodiments of the present invention have the general formula (I)

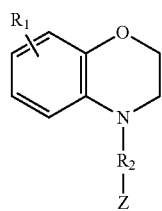

(I)

Herein $R_1$ is selected from H and halogens, $R_2$ is selected from H, an amide, or a carbamate, and Z is selected from a $C_1$-$C_4$ alkyl and a substituted or unsubstituted phenyl group.

Exemplary compounds of formula (I) where Z is methyl, tertiary butyl, phenyl, and benzyl are described below.

Exemplary embodiments of the present invention illustrate the synthesis of un-protected benzoxazines. 2-amino phenol derivatives reacted with a bromoethylsulfonium salt or diphenyl vinyl sulfonium triflate provided the unprotected benzoxazines shown in the following Scheme 1. The formation of aziridine was not observed as the formation of aziridine happens primarily in the case of un-protected β-amino alcohol.

Scheme 1: Synthesis of unprotected benzoxazines from sulfonium salts

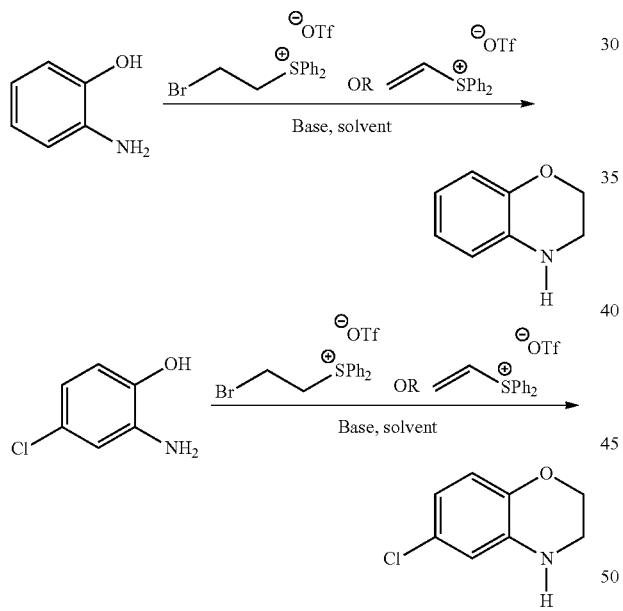

An exemplary group of compounds are those of formula I:

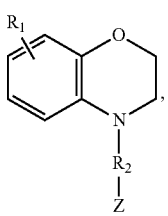

(I)

where $R_1$ is H or Cl, and $R_2$ is H.

Exemplary compounds of the present invention are:
3,4-dihydro-2H-benzo[b][1,4]oxazine; and
6-chloro-3,4-dihydro-2H-benzo[b][1,4]oxazine.

Exemplary compounds of the present invention are also:
tert-butyl 2H-benzo[b][1,4]oxazine-4(3H)-carboxylate;
tert-butyl 6-chloro-2H-benzo[b][1,4]oxazine-4(3H)-carboxylate;
benzyl 2H-benzo[b][1,4]oxazine-4(3H)-carboxylate;
benzyl 6-chloro-2H-benzo[b][1,4]oxazine-4(3H)-carboxylate;
1-(2H-benzo[b][1,4]oxazin-4(3H)-yl)ethanone; and
(2H-benzo[b][1,4]oxazin-4(3H)-yl)(phenyl)methanone.

The exemplary compounds of formula (I) above may be prepared by reacting a compound of formula (II):

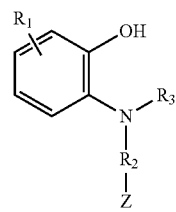

(II)

with compounds:

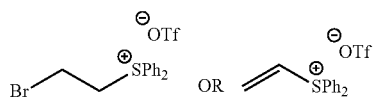

in an organic solvent such as dichloromethane (DCM), tetrahydrofuran (THF), chloroform, and acetonitrile (CAN) at room temperature (25-30° Celsius), in the presence of a base, for example sodium hydride (NaH).

The compounds of formula (II), according to the present exemplary embodiment, may be prepared by reacting a compound of formula:

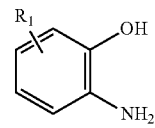

with one or more compounds of formulas:

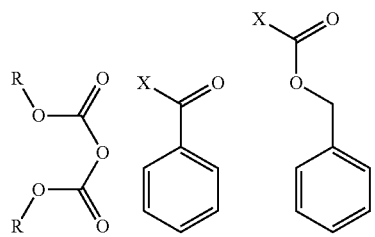

Here, $R_1$ are each independently selected from H and a halogen, where X is a halogen, for example, fluorine, chlorine, or bromine.

Synthesis of phenol derivatives containing N—BOC (butyloxycarbonyl), N-Cbz (benzyloxy carbonyl), N-Ac (acetyl), and N-Bz (benzoyl) protecting groups has been accomplished according to the present exemplary embodiment. The N-protected phenol derivatives were formed in excellent yields from o-amino phenols under simple reaction conditions. The products were then purified with appropriate solvent washings without column chromatography.

Exemplary embodiments of the present invention also provide synthesis methods using an N-Boc protected amino phenol substrate that is treated with a bromoethyl sulfonium salt and a base. 3.5 equivalents of a strong base, such as NaH, produced 3,4-dihydro-2H-1,4-benzoxazine in excellent yields at room temperature (RT), in 5 hours, whereas the weak base such as DIPEA (diisopropylethylamine) substantially did not produce any product. $^1$H NMR (nuclear magnetic resonance) of the crude material revealed the presence of benzoxazine exclusively. Purification of benzoxazines may be achieved by washing the product with n-hexane. Table 1 shows the yields of benzoxazines using different listed bases.

TABLE 1

Bases used and Yield of Benzoxazine

| Entry | Base | Yield (%) |
|---|---|---|
| 1 | NaH | 99 |
| 2 | DBU (1,8-diazabicyclo[5.4.0]undec-7-ene) | 42 |
| 3 | DIPEA (diisopropylethylamine) | 0 |
| 4 | Nat-OBu (sodium tertiary butoxide) | 72 |

Exemplary embodiments of the present invention utilize a bromoethyl sulfonium salt as a dialkylating agent that may not have been used for transformations.

Exemplary embodiments of the present invention may work efficiently with amide and carbamate nitrogen protecting groups. However, previously reported compounds including β-amino alcohols having nitrogen protected by amide and carbamate groups did not undergo required annulation reactions using a diphenyl vinyl sulfonium salt.

Thus, exemplary embodiments of the present invention disclose synthesis of biologically important benzoxazines in high yields and under mild reaction conditions.

Substrates bearing sulfonamides worked well when used in presence of sulfonium salts. However, amides and carbamates did not give the required products. Whereas a number of pharmaceutical drugs contain amide and carbamate moieties, exemplary embodiments of the present invention allow the use of amides and carbamates when using a diphenyl vinyl sulfonium salt.

Previous methods suffered from low yields, long reaction times, and expensive reagents. However, exemplary embodiments of the present invention allow for high yields even for amides and carbamates.

Exemplary embodiments of the present invention demonstrate the scope of the reaction in a range of substrates bearing amide and carbamate functional groups that were reacted with a bromoethyl sulfonium salt or a diphenyl vinyl sulfonium salt, which generate corresponding 1,4-benzoxazines in excellent yields. After the successful synthesis of Boc protected benzoxazine, the method was extended to the synthesis of N-Cbz protected benzoxazines. N-Cbz protected phenols and a bromoethyl sulfonium salt yielded N-Cbz benzoxazines under the reaction conditions, in excellent yields. N-Ac and N-Bz protected benzoxazines may also be effectively synthesized using this process. The overall scope of the present exemplary embodiment for compounds of formula (I) is indicated in the following reaction Scheme 2.

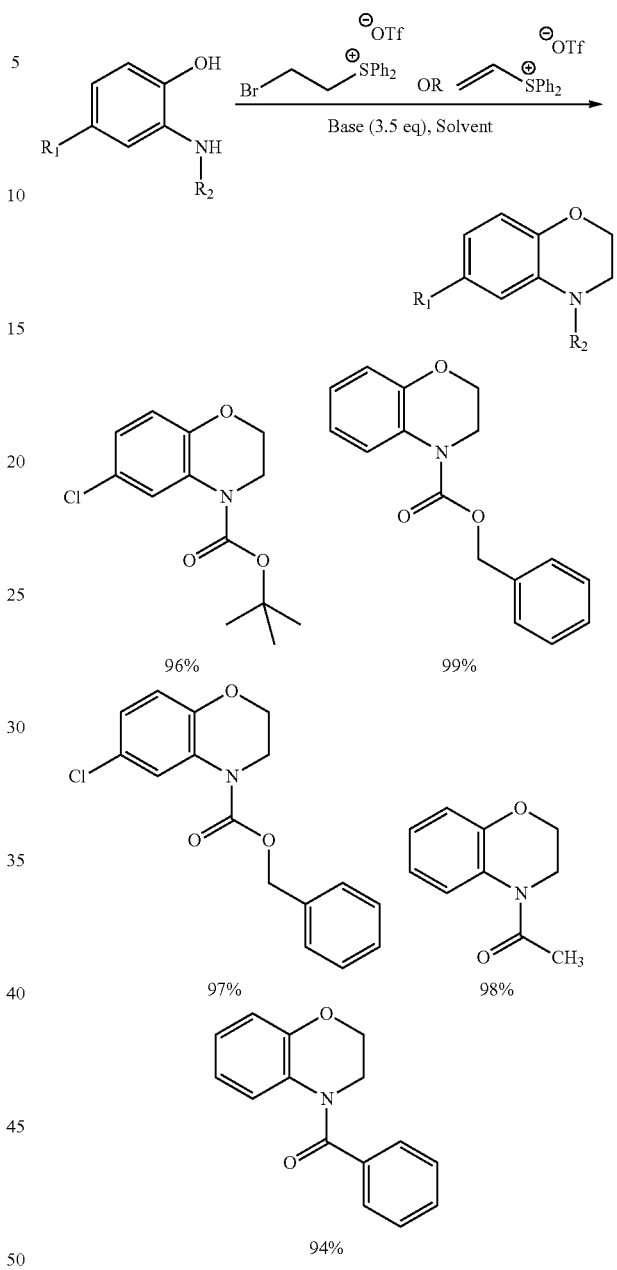

Scheme 2: Examples demonstrating the scope of new methodology

Exemplary embodiments provide for the concise synthesis of amides, N—BOC, N-Cbz, and un-protected benzoxazines from the corresponding phenol derivatives and a bromoethyl sulfonium salt or a diphenyl vinyl sulfonium salt. This simple, one-step protocol substantially avoids any side products, making it compatible with a much broader range of functional groups.

Hereinafter, exemplary embodiments of the present invention will be described in greater detail by way of specific examples.

Example 1

Tert-butyl 2-hydroxyphenylcarbamate

Di-tert-butyldicarbonate (11 mmol) was added to a stirred solution of 2-aminophenol (10 mmol) in dry THF (15 mL).

The reaction mixture was stirred for 15 hours at room temperature (RT) under a nitrogen atmosphere. Then, the solvent was evaporated under vacuum and the resulting reaction mixture was washed with pentane (20 mL) and dissolved into diethyl ether (30 mL). Diethyl ether portion was washed with diluted HCl (10 mL), then dried over $Na_2SO_4$ and filtered. On evaporation under vacuum the targeted compound was obtained as a white solid (80%).

$^1$H NMR data were: δH (500 MHz; $CDCl_3$) 8.17 (1H, s, H—N), 7.11-6.81 (4H, m, ArH), and 1.52 (9H, s, $CH_3$); and δc (500 MHz; $CDCl_3$) 155.0 (C=O), 147.2 (C), 125.8 (C), 121.6 (CH), 120.7 (CH), 118.6 (CH), 82.0 (C), and 28.35 ($CH_3$).

Example 2

Tert-butyl 5-chloro-2-hydroxyphenylcarbamate

Di-tert-butyldicarbonate (11 mmol) was added to a stirred solution of 2-amino-4-chlorophenol (10 mmol) in distilled water (30 mL) the reaction mixture was further stirred for 15 hours at RT. The product was filtered, washed with water to give the targeted compound (88%) as a white solid.

$^1$H NMR data were: δH (500 MHz; $CDCl_3$) 7.79-6.85 (3H, m, ArH), and 1.55 (9H, s, $CH_3$); and δc (500 MHz; $CDCl_3$) 154.5 (C=O), 145.7 (C), 126.6 (CH), 125.4 (C), 124.9 (C), 120.8 (CH), 119.4 (CH), 82.4 (C), and 28.2 ($CH_3$).

Example 3

Benzyl 2-hydroxyphenylcarbamate

Benzyl chloroformate (11 mmol, 58% in toluene) was added drop wise to a stirred solution of 2-aminophenol in $NaHCO_3$ (3M, 3.6 mL). The reaction mixture was further stirred for 15 hours at RT. Then the reaction mixture was washed with NaOH (3M, 20 mL) followed by water (20 mL) and diethyl ether (20 ml×3). Concentrated HCl was added to the aqueous part until precipitation of the targeted product as a light yellow solid (70%).

$^1$H NMR data were: δH (500 MHz; $CDCl_3$) 7.40-6.86 (9H, m, ArH), and 5.23 (2H, s, $CH_2$—O); and δc (500 MHz; $CDCl_3$) 155.2 (C=O), 146.8 (C), 135.4 (C), 128.7 (CH), 128.6 (CH), 128.4 (CH), 125.6 (CH), 125.2 (CH), 121.2 (CH), 121.0 (CH), 118.3 (C), and 68.1 ($CH_2$).

Example 4

Benzyl 5-chloro-2-hydroxyphenylcarbamate

Benzyl chloroformate (11 mmol, 58% in toulene) was added drop wise to a stirred solution of 2-amino-4-chlorophenol (10 mmol) in 3M solution of $NaHCO_3$ (3.6 mL), then distilled water (10 ml) was added and the reaction mixture was stirred at RT for 15 hours. Then the reaction mixture was washed with NaOH (3M, 20 mL) followed by water (20 mL) and diethyl ether (20 ml×3). Concentrated HCl was added to the aquous part resulting in precipitation of the targeted product as a light brown solid (79%).

$^1$H NMR data were: δH (500 MHz; DMSO) 10.1 (1H, br s, H—O), 8.58 (1H, s, H—N), 7.67-6.81 (8H, m, ArH), and 5.13 (2H, s, $CH_2$-Ph); and δc (500 MHz; DMSO) 153.6 (C=O), 146.7 (C), 136.6 (C), 128.4 (CH), 128.0 (CH), 127.9 (C), 127.3 (C), 123.4 (CH), 122.2 (CH), 120.7 (CH), 116.3 (CH), and 65.9 ($CH_2$).

Example 5

N-(2-hydroxyphenyl) acetamide

Acetic anhydride (11 mmol) was added drop wise to a vigorously stirred suspension of 2-aminophenols (10 mmol) in water (10 mL). The reaction mixture was stirred for 30 min after the addition was complete. The mixture was filtered through a buchner funnel, and on drying in vacuum, the targeted compound was obtained as white solid.

Melting point of the targeted compound was 208-209° C., and yield was 91%.

$^1$H NMR data were: δH (500 MHz; DMSO) 9.29 (1H, s, H—N), 7.65-6.72 (4H, m, ArH), and 2.07 (3H, s, $CH_3$); and δc (500 MHz; DMSO) 169.1 (C=O), 147.9 (C), 126.4 (C), 124.7 (CH), 122.4 (CH), 119.0 (CH), 115.9 (CH), and 23.6 ($CH_3$).

Example 6

N-(2-hydroxyphenyl)benzamide

Benzoyl chloride (11 mmol) was added drop wise to a stirred solution of 2-aminophenol (10 mmol) in aqueous $NaHCO_3$ solution (3M, 3.6 mL) at RT. The reaction mixture was further stirred at RT for 15 hours. The product was precipitated out, filtered, washed with water, and dried, and the targeted compound was obtained as a white solid (77%).

$^1$H NMR data were: δH (500 MHz; $CDCl_3$) 8.62 (1H, s, H—N), and 8.10-6.91 (9H, m, ArH); and δc (500 MHz; $CDCl_3$) 167.1 (C=O), 148.7 (C), 133.1 (C), 132.5 (CH), 128.9 (CH), 128.9 (CH), 127.3 (CH), 127.3 (CH), 125.6 (C), 122.3 (CH), 122.2 (CH), 120.6 (CH), and 119.8 (CH).

General procedure "A" for synthesis of benzoxazines:

A stifling solution of the requisite phenol derivative, (10 mmol) in $CH_2Cl_2$ (20 mL) was treated with NaH (35 mmol) at 0° C. under argon. After 5 minutes, 2-bromoethyldiphenyl-sulfonium salt (12 mmol) was added and the reaction was stirred for 5 hours at RT. The reaction was then quenched with saturated ammonium chloride solution (10 mL), and extraction was performed with $CH_2Cl_2$ (3×25 mL), washed with brine (20 mL), the resultant was dried over $MgSO_4$, filtered and concentrated under vacuum. The targeted compound was then purified using chromatography on silica.

Example 7

Tert-butyl 2H-benzo[b][1,4]oxazine-4(3H)-carboxylate

Following general procedure A, yield was 99%, melting point was 72-74° C. (Ethyl acetate: Pet ether; compared to literature value of 73-75° C.).

$^1$H NMR data were: δH (500 MHz; $CDCl_3$) 7.79-6.85 (4H, m, ArH), 4.23 (2H, br s, $CH_2$—O), 3.85 (2H, br s, $CH_2$—N), and 1.54 (9H, s, $CH_3$); and δc (500 MHz; $CDCl_3$) 152.5 (C=O), 145.8 (C), 126.1 (C), 124.3 (CH), 123.5 (CH), 120.1 (CH), 116.9 (CH), 81.6 (C), 65.5 ($CH_2$), 42.0 ($CH_2$), and 28.3 ($CH_3$).

Mass spectrometry (MS) m/z (EI) 235; HRMS calcd for $C_{13}H_{17}NO_3$ (M+) 235.1208, obsd 235.1198.

Example 8

Tert-butyl 6-chloro-2H-benzo[b][1,4]oxazine-4(3H)-carboxylate

Following general procedure A, yield was 96%.

$^1$H NMR data were: δH (500 MHz; CDCl$_3$) 7.88-6.78 (3H, m, ArH), 4.21 (2H, t, J 5, CH$_2$—O), 3.83 (2H, t, J 4.9, CH$_2$—N), and 1.55 (9H, s, CH$_3$); and δc (500 MHz; CDCl$_3$) 152.1 (C=O), 144.4 (C), 126.9 (C), 125.0 (C), 124.0 (CH), 123.0 (CH), 117.8 (CH), 82.2 (C), 65.2 (CH$_2$), 42.0 (CH$_2$), and 28.2 (CH$_3$).

MS m/z (EI) 269; HRMS calcd for C$_{13}$H$_{16}$NO$_3$Cl (M+) 269.0819, obsd 269.0812.

Example 9

Benzyl 2H-benzo[b][1,4]oxazine-4(3H)-carboxylate

Following general procedure A, yield was 99%.

$^1$H NMR data were: δH (500 MHz; CDCl$_3$) 7.85-6.86 (9H, m, ArH), 5.25 (2H, s, CH$_2$-Ph), 4.24 (2H, t, J 4.5, CH$_2$—O), and 3.93 (2H, t, J 4.5, CH$_2$—N); and δc (500 MHz; CDCl$_3$) 153.4 (C=O), 146.0 (C), 136.0 (CH), 128.6 (CH), 128.3 (CH), 128.1 (CH), 125.7 (C), 124.8 (CH), 123.2 (C), 120.5 (CH), 117.1 (CH), 67.9 (CH$_2$), 65.4 (CH$_2$), and 42.5 (CH$_2$).

MS m/z (EI) 269; HRMS calcd for C$_{16}$H$_{15}$NO$_3$ (M+) 269.1052, obsd 269.1049.

Example 10

Benzyl 6-chloro-2H-benzo[b][1,4]oxazine-4(3H)-carboxylate

Following general procedure A, yield was 97%.

$^1$H NMR data were: δH (500 MHz; CDCl$_3$) 7.97-6.79 (8H, m, ArH), 5.27 (2H, s, CH$_2$-Ph), 4.22 (2H, t, J 4.5, CH$_2$—O), and 3.91 (2H, t, J 4.5, CH$_2$—N); and δc (500 MHz; CDCl$_3$) 153.0 (C=O), 144.5 (C), 135.6 (C), 128.7 (CH), 128.6 (CH), 128.4 (CH), 128.3 (CH), 128.1 (CH), 126.3 (C), 125.2 (CH), 124.5 (C), 122.7 (CH), 122.7 (CH), 118.0 (CH), 68.1 (CH$_2$), 65.1 (CH$_2$), and 42.2 (CH$_2$).

MS m/z (EI) 303; HRMS calcd for C$_{16}$H$_{14}$NO$_3$Cl (M+) 303.0662, obsd 303.0653.

Example 11

1-(2H-benzo[b][1,4]oxazin-4(3H)-yl)ethanone

Following general procedure A, yield was 98%, melting point was 58-60° C. (Ethyl acetate: Pet ether; compared to literature value of 59-60° C.).

$^1$H NMR data were: δH (500 MHz; CDCl$_3$) 7.1-6.7 (4H, m, ArH), 4.3 (2H, br s, CH$_2$—O), 3.8 (2H, br s, CH$_2$—N), and 2.04 (3H, s, CH$_3$); and δc (500 MHz; CDCl$_3$) 169.1 (C=O), 147 (C), 126.4 (C), 124.3 (CH), 122(CH), 120.2 (CH), 117.2 (CH), 67.1 (CH$_2$), 39.4 (CH$_2$), and 23.0 (CH$_3$).

MS m/z (EI) 177; HRMS calcd for C$_{10}$H$_{11}$NO$_2$ (M+) 177.0790, obsd 177.0781.

Example 12

(2H-benzo[b][1,4]oxazin-4(3H)-yl)(phenyl)methanone 2f

Following general procedure A, yield was 94%, melting point was 107-109° C. (Ethyl acetate: Pet ether; compared to literature value of 109-110° C.

$^1$H NMR data were: δH (500 MHz; CDCl$_3$) 7.51-6.64 (9H, m, ArH), 4.37 (2H, t, J, CH$_2$—O), and 4.00 (2H, t, J, CH$_2$—N); and δc (500 MHz; CDCl$_3$) 168.7 (C=O), 146.1 (C), 135.1 (C), 130.6 (CH), 128.4 (CH), 128.4 (CH), 126.0 (C), 125.5 (CH), 124.3 (CH), 119.8 (CH), 119.8 (CH), 117.1 (CH), 66.4 (CH$_2$), and 42.5 (CH$_2$).

MS m/z (EI) 239; HRMS calcd for C$_{15}$H$_{13}$NO$_2$ (M+) 239.0946, obsd 239.0945.

Example 13

3,4-dihydro-2H-benzo[b][1,4]oxazine

Following general procedure "A", in the case of un-protected benzoxazines the procedure was modified:

After 15 hours stifling at RT, the reaction was then quenched with distilled water (10 mL), HCl was added until pH around 4 was reached, then extraction was performed with diethyl ether (2×10 ml), the diethyl ether portion was then discarded. Then a NaHCO$_3$ solution (3M) was added until a pH 10 was reached, extraction was performed with CH$_2$Cl$_2$ (3×10 mL), the resultant was dried over MgSO$_4$, filtered and concentrated under vacuum. The product was then purified using chromatography on silica. The yield was 68%.

$^1$H NMR data were: δH (500 MHz; CDCl$_3$) 6.78-6.59 (4H, m, ArH), 4.25 (2H, t, J 4.6, CH$_2$—O), 3.48 (1H, s, H—N), and 3.42 (2H, t, J 4.2, CH$_2$—N); and δc (500 MHz; CDCl$_3$) 144.1 (C), 133.5 (C), 121.2 (CH), 118.8 (CH), 116.7 (CH), 115.6 (CH), 65.2 (CH$_2$), and 40.9 (CH$_2$).

MS m/z (EI) 135; HRMS calcd for C$_8$H$_9$NO (M+) 135.0684, obsd 135.0677.

Example 14

6-chloro-3,4-dihydro-2H-benzo[b][1,4]oxazine

Following general procedure "A", in the case of un-protected benzoxazines the procedure was modified:

After 15 hours stifling at RT, the reaction was then quenched with distilled water (10 mL), HCl was added until pH around 4 was reached, then extraction was performed with diethyl ether (2×10 ml), the diethyl ether portion was then discarded. Then a NaHCO$_3$ solution (3M) was added until a pH 10 was reached, extraction was performed with CH$_2$Cl$_2$ (3×10 mL), the resultant was dried over MgSO$_4$, filtered and concentrated under vacuum. The targeted product was then purified using chromatography on silica. Yield was 73%.

$^1$H NMR data were: δH (500 MHz; CDCl$_3$) 6.68-6.55 (3H, m, ArH), 4.21 (2H, br s, CH$_2$—O), 3.71 (1H, s, H—N), and 3.48-3.40 (2H, m, CH$_2$—N); and δc (500 MHz; CDCl$_3$) 142.5 (C), 134.5 (C), 118.2 (C), 117.5 (CH), 117.2 (CH), 114.8 (CH), 65.0 (CH$_2$), and 40.5 (CH$_2$).

MS m/z (EI) 169; HRMS calcd for C$_8$H$_8$NOCl (M+) 169.0294, obsd 169.0292.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A compound comprising formula (II):

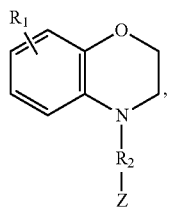 (II)

wherein:
R1 is selected from the group consisting of Cl, I, and F;
R2 consists of

and
Z consists of t-butyl.

2. A compound comprising formula (II):

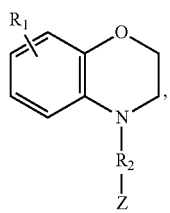 (II)

wherein:
R1 consists of Cl;
R2 consists of

and
Z consists of benzyl.

3. A method of preparing compounds of formula (II):

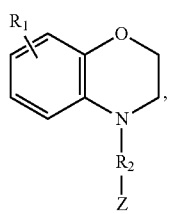 (II)

wherein:
R1 is selected from the group consisting of H and a halogen;
R2 is selected from the group consisting of

and

and
Z is selected from the group consisting of a phenyl, benzyl, methyl, and t-butyl,
the method comprising:
reacting a substituted amino phenol and with bromo ethyl sulfonium triflate in the presence of a base comprising at least one of sodium hydride, 1,8-diazabicyclo[5.4.0]undec-7-ene (DBU), sodium tertiary butoxide, in a solvent comprising at least one of dicholoromethan, tetrahydrofuran, cholorform, and acetonitrile, at a temperature in the range of 25 to 30 degrees Celsius.

4. The method of claim 3, wherein preparing the compound of formula (II) further comprises reacting an N-protected amino phenol derivative with bromo ethyl sulfonium triflate in the presence of NaH, in a solvent comprising at least one of dicholoromethane, tetrahydrofuran, cholorform, and acetonitrile, at a temperature in the range of 25 to 30 degrees Celsius.

5. The method of claim 3, wherein:
R1 is selected from the group consisting of Cl, I, and F;
R2 consists of

and
Z consists of t-butyl.

6. The method of claim 3, wherein:
R1 consists of Cl;
R2 consists of

and
Z consists of benzyl.

* * * * *